United States Patent [19]

McCarthy

[11] Patent Number: 4,995,869
[45] Date of Patent: Feb. 26, 1991

[54] MONO-USE SYRINGE FOR HYPODERMIC INJECTIONS

[75] Inventor: Martin McCarthy, Milan, Italy

[73] Assignee: Clyde Fessler, Milwaukee, Wis.

[21] Appl. No.: 419,022

[22] Filed: Oct. 10, 1989

[30] Foreign Application Priority Data

Dec. 21, 1988 [IT] Italy ................................ 23040 A/88

[51] Int. Cl.⁵ ................................................ A61M 5/00
[52] U.S. Cl. ..................................... 604/110; 604/220
[58] Field of Search ............... 604/110, 187, 218, 220, 604/208, 210

[56] References Cited

U.S. PATENT DOCUMENTS

| | | | |
|---|---|---|---|
| 4,367,738 | 1/1983 | Legendre et al. ............. | 604/218 X |
| 4,642,102 | 2/1987 | Ohmori ............................... | 604/220 |
| 4,731,068 | 3/1988 | Hesse ................................... | 604/110 |
| 4,826,483 | 5/1989 | Molnar, IV .......................... | 604/110 |

Primary Examiner—John D. Yasko
Attorney, Agent, or Firm—Michael, Best & Friedrich

[57] ABSTRACT

The disclosure provides a syringe for hypodermic injections having a needle and including a barrel defining a chamber in fluid communication with the needle, a guide member disposed within the chamber, a plunger disposed within the chamber and between the guide member and the needle, the plunger having a stem extending through the guide member, and first means for allowing movement of the guide member relative to the barrel in one direction and for preventing return movement of the guide member and second means for allowing movement of the plunger relative to the guide member and for preventing return movement of the plunger, the second means including lost motion means to permit limited return movement of the plunger so that the user can determine that injection into a vein has been achieved.

10 Claims, 1 Drawing Sheet

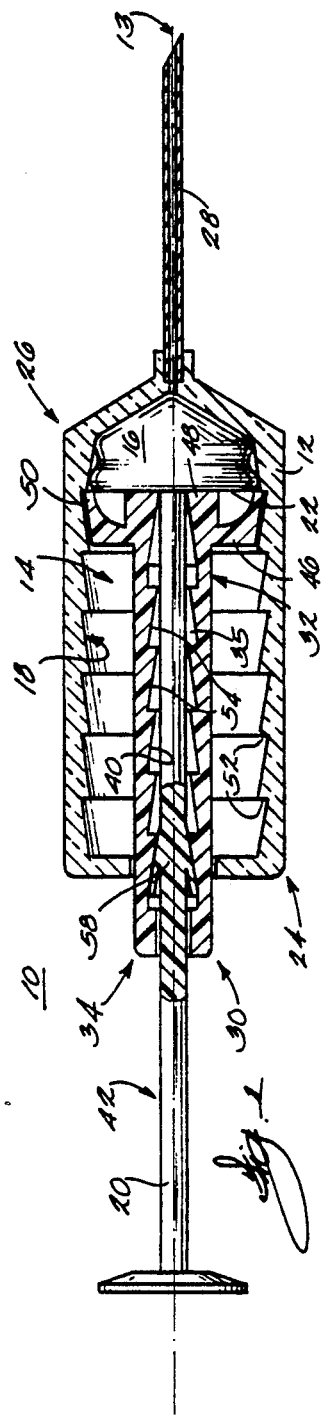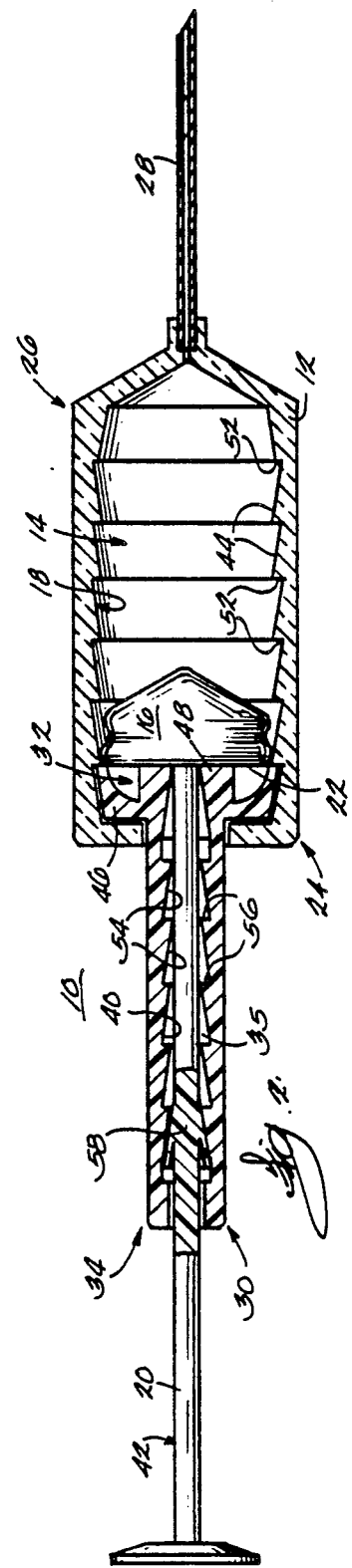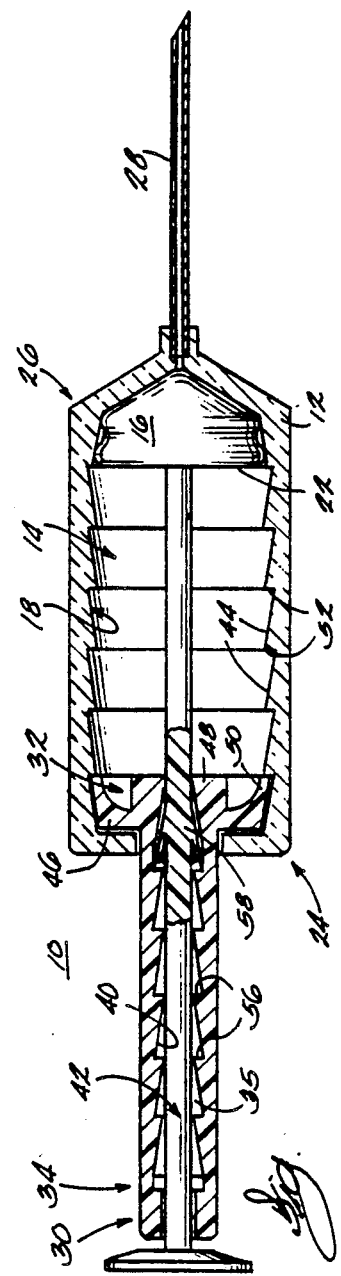

MONO-USE SYRINGE FOR HYPODERMIC INJECTIONS

BACKGROUND OF THE INVENTION

The invention relates to syringes suited for hypodermic injections and more particularly to mono-use syringes for hypodermic injections.

The use of mono-use "throw-away" syringes is known. Typically, "throw-away" syringes are packaged singularly in hermetically sealed wrappers. This simple type of packaging is practical and guarantees sterility of the syringe up until the moment that the syringe is used.

A problem associated with "throw-away" syringes is the possibility of reuse of the syringe for further injections. Because there is no assurance of hygienic conditions, repeated use of "throw-away" syringes increases risk of transmission of various types of diseases. The problems associated with the repeated use of "throw-away" syringes has been well documented in the case of intravenous drug abusers who commonly use syringes previously used by others.

The use of mono-use syringes having various mechanisms to render the syringe inoperable after a single use is also known. Examples of prior art mono-use syringes are illustrated in the following patents: Yerman U.S. Pat. No. 4,233,975 issued to on Nov. 18, 1980; Legendre U.S. Pat. No. 4,367,738 on Jan. 11, 1983; Butterfield U.S. Pat. No. 4,493,703 on Jan. 15, 1985; Hesse U.S. Pat. No. 4,731,068 on Mar. 15, 1988; and British Patent 2,197,792A published on June 2, 1988.

In the course of medical treatment, the intravenous nature of an injection is often important, as where the injected solution is toxic to muscle tissue or where the effectiveness of the treatment requires direct absorption of the injected solution by the blood stream. A commonly practiced technique used to verify the positive puncturing of a vein is by withdrawing a small amount of blood after the contents of the syringe have been injected.

SUMMARY OF THE INVENTION

It is an object of the invention to provide a mono-use syringe for hypodermic injections having a mechanism which renders the syringe inoperable after a single use.

It is a further objective of the invention to provide a mono-use syringe having a simplified design for facilitation of its manufacture and reliability in operation.

It is a further object of the invention to provide a mono-use syringe which facilitates the verification of an injection as being intraveneous.

The invention provides a syringe for hypodermic injections having a needle and including a barrel defining a chamber in fluid communication with the needle, a guide member disposed within the chamber, a plunger disposed within the chamber and between the guide member and the needle, the plunger having a stem extending through the guide member, and first means for allowing movement of the guide member relative to the barrel in one direction and for preventing return movement of the guide member and second means for allowing movement of the plunger relative to the guide member and for preventing return movement of the plunger, the second means including lost motion means to permit limited return movement of the plunger so that the user can determine that injection into a vein has been achieved.

In the preferred embodiment, the first means includes first ratchet means located on the guide member and on the barrel for allowing movement of the plunger and the guide member to a remote position relative to the needle and for preventing return movement of the guide member, the second means includes second ratchet means located on the guide member and the stem for allowing movement of the plunger relative to the guide member in the direction of the needle and for preventing movement of the plunger relative to the guide member in the direction away from the needle.

In one embodiment of the invention, the first ratchet means includes at least one first ratchet member on the barrel and at least one first flexible pawl member on the guide member, the first flexible pawl members being adapted to move over the first ratchet members in a first direction and to engage the first ratchet members to prevent movement of the guide member in an opposite direction. The second ratchet means includes at least one second ratchet member on the guide member and at least one second flexible pawl member on the plunger, the second flexible pawl members being adapted to move over the second ratchet members in a first direction and to engage the second ratchet members to prevent movement of the guide member in an opposite direction.

According to a more specific aspect of the invention, the first ratchet members each include a frusto-conical section extending into the chamber, the first ratchet members tapering inwardly and away from the needle and having a ratchet step facing in a direction away from the needle. The first flexible pawl members slidably engage the first ratchet members and engage the ratchet step on the first ratchet members. The guide member includes a bore, and the second ratchet members each include a frusto-conical section extending into the bore. The second ratchet members taper inwardly and have a ratchet step facing toward the needle. The second flexible pawl members slidably engage the second ratchet members and engage the ratchet step one each of the second ratchet members.

In order to facilitate the verification of an intravenous injection, a feature of the invention is the provision of ratchet members on both the barrel and the guide member. The blocking action of the ratchet members on the barrel and on the guide member prevents movement of the syringe in opposite directions. This provision of counter-directional blocking allows the slight withdrawal of the plunger for the aspiration of blood to verify the intravenous nature of the injection.

Various other features and advantages of the invention will become apparent to those skilled in the art upon review of the following detailed description, claims and drawings.

DESCRIPTION OF THE DRAWINGS

FIG. 1 is a cross sectional view of a syringe embodying the invention.

FIG. 2 is a cross sectional view of the syringe illustrated in FIG. 1 with the plunger withdrawn to its extreme remote position.

FIG. 3 is a cross sectional view of the syringe illustrated in FIG. 1 with the plunger in its fully injected position.

DESCRIPTION OF THE PREFERRED EMBODIMENT

The mono-use syringe 10 according to the preferred embodiment of the invention, includes a generally cylindrical barrel 12 having an axis 13 and which defines a reservoir chamber 14. A piston 16 is disposed for axial movement within the chamber 14 and is circumferentially compressed to sealingly engage the chamber's inner surface 18. A stem 20 is attached to one side 22 of the piston 16 and extends axially from one end 24 of the barrel 12. At the other end 26 of the barrel 72, there is a needle 28 which is in fluid communication with the chamber 14. In addition, there is a guide 30 having a first portion 32 disposed within the chamber 14 and between the piston 16 and the one end and a second portion 34 extending outwardly from the one end 24 of the barrel 12 and having a bore 35 in surrounding relation to the stem 20.

The inner surface of the barrel 18 and the first guide portion 32 define a first ratchet means which permits the guide 30 and the piston 16 to move from the needle end 26 to the remote end 24 of the chamber 14 but prevent return movement of the guide 30. A second ratchet means is defined by the inner surface 40 of the second guide portion 34 and the outer surface 42 of the stem 20 for permitting return movement of the piston 16 toward the needle end 26 of the chamber 14 but prevent subsequent movement of the piston 16 away from the needle 28 except for slight movement to verify that the injection was intravenous.

In the illustrated embodiment, the first ratchet means includes a plurality of equal, coaxial, frusto-conical sections 44 formed on the inner surface 18 of the barrel 12 and arranged end to end which, in cross section, gives the chamber 14 a saw tooth profile.

The first guide portion 32 defines a first pawl 46 and includes an inner hub 48 and a skirt 50 extending therefrom. The outer periphery of the skirt 50 is frusto-conical and complementary to the sections 44 on the barrel 12 and is oriented in the same direction. The skirt portion 50 of the first pawl member 46 is formed of a generally flexible material and is adapted to flex so as to permit sliding movement over the conical sections 44 in a direction away from the needle 28, and to engage the shoulders 52 between the conical sections 44 to prevent movement in a direction towards the needle 28.

The second ratchet means includes a plurality of equal and coaxial frusto-conical sections 54 formed in end to end relation on the inside of the bore 35 of the guide member 30. Each of the second conical sections defines a second ratchet step 56 which lies in a plane generally perpendicular to the axis 13 of the barrel 12.

The second ratchet means also includes at least one second pawl member 58 located on the stem 20. In the illustrated embodiment, the second pawl member 58 is a hollow conical section attached to the stem 58 intermediate its ends and is disposed within the bore 35. The second pawl member 58 is also formed of a flexible plastic material and is adapted to slidably move over the second ratchet members 54 in a direction relative to the guide member toward the needle 28, but engages the second ratchet step 56 when moved in a direction away from the needle 28. The length of the second pawl member 58 is shorter in the axial direction than the conical sections 54 to permit a slight movement of the piston 16 away from the needle 28.

As shown in FIG. 1, the mono-use syringe 12 is originally constructed so that the piston 16, and the guide member 30 are positioned to the extreme right hand end of the chamber 14. As shown in FIG. 2, the piston 16 and stem 20 may be extracted to a remote position on the extreme end of the chamber away from the needle end 26 of the barrel. Retraction of the stem 20 causes the piston head 16 to move the guide member 30 to the remote position. During retraction of the stem 20, the first flexible pawl member 46 slidably engages the first ratchet members 44 and moves over the ratchet members 44 to the remote position.

During injection of solution which is drawn into the chamber, the piston head 16 forces fluid from the chamber 14 through the needle 28. As the piston 16 is moved towards the needle end 26 of the chamber 14, the first pawl members 46 engage the first ratchet step 52 and prevent the guide member 30 from returning to its original position. Thus, the guide member 30 is restricted from movement away from the remote position. As the piston 16 is moved towards the needle end 26 of the chamber 14, the second pawl member 58 slidably moves over the second ratchet members 54. As shown in FIG. 3, once the piston head 16 has reached the needle end 26 of the chamber 16, the solution in the chamber 14 has been forced out of the chamber 14 through the needle 28.

Because it is sometimes necessary to verify that the injection has an intravenous nature, the invention provides for slight retraction of the piston head 16 so as to aspirate a small amount of blood. The second flexible pawl member 58 is allowed to move back along the second ratchet member 54 before it engages the second ratchet step 56. Upon engaging the second ratchet step 56, the second pawl member 58 can no longer move relative to the guide member 30 in a direction away from the needle 28. The mono-use syringe 10 is thus rendered inoperable after a single use.

I claim:

1. A syringe for hypodermic injections having a needle, the syringe comprising
    a barrel defining a chamber in fluid communication with the needle,
    a guide member disposed within the chamber,
    a plunger disposed within the chamber and between the guide member and the needle, the plunger having a stem extending through the guide member,
    first ratchet means on the guide member and one the barrel for allowing movement of the guide member and plunger to a remote position relative to the needle and for preventing return movement of the guide member, and
    second ratchet means on the guide member and the stem for allowing movement of the plunger relative to the guide member in the direction of the needle and for preventing movement of the plunger relative to the guide member in the direction away from the needle.

2. A syringe as set forth in claim 1 wherein the first ratchet means includes at least one first ratchet member on the barrel and at least one first flexible pawl member on the guide member, the first flexible pawl members being adapted to move over the first ratchet members in a first direction and to engage the first ratchet members to prevent movement of the guide member in an opposite direction, and wherein the second ratchet means includes at least one second ratchet member on the guide member and at least one second flexible pawl member on the plunger, the second flexible pawl members being adapted to move over the second ratchet members in a first direction and to engage the second ratchet members to prevent movement of the guide members in an opposite direction.

3. A syringe as set forth in claim 2 wherein the chamber has two ends and the barrel supports the needle on one end of the chamber, and wherein the first flexible pawl members engage the first ratchet members to prevent movement in the direction toward the needle, and wherein the second flexible pawl members engage the second ratchet members to prevent movement in a direction away from the needle.

4. A syringe as set forth in claim 4 wherein the first ratchet members each comprise a frusto-conical section formed on the inner surface of the barrel, the first ratchet members tapering inwardly and having their large diameters toward the needle to define ratchet steps facing in a direction away from the needle, and wherein the first flexible pawl members slidably engage the first ratchet members and engage the ratchet step on each of the first ratchet members.

5. A syringe as set forth in claim 4 wherein the guide member has a bore, and wherein the second ratchet members each include a frusto-conical section formed on the surface of the bore, the second ratchet members tapering inwardly and having a ratchet step facing toward the needle, and wherein the second flexible pawl members slidably engage the second ratchet members and engage the ratchet step on each of the second ratchet members.

6. A syringe as set forth in claim 1 wherein said second ratchet means includes lost motion means to permit limited movement of said plunger away from the needle so that intraveneous injections can be confirmed.

7. A syringe as set forth in claim 5 wherein the length of the second flexible pawl member is shorter than the conical sections to permit limited movement of the plunger away from the needle so that intraveneous injections can be confirmed.

8. A syringe for hypodermic injections comprising
a barrel defining a chamber having at least one frusto-conical section and supporting a needle adapted for hypodermic injections in fluid communication with the chamber,
a guide member disposed within the chamber and having a outer surface including a frusto-conical portion adapted to engage each of the frusto-conical sections in the chamber, the guide member having a bore including at least one frusto-conical section, and
a plunger having a first portion disposed within the chamber and extending into the bore, the shaft having at least one conical section adapted to engage each of the frusto-conical sections in the bore.

9. A syringe as set forth in claim 8 wherein each frusto-conical section in the chamber tapers inwardly and away from the needle and defines a ratchet step in the chamber, each frusto-conical section in the bore tapering inwardly and toward needle and defining a ratchet step in the bore, said guide member having a shoulder engagable with each ratchet step on the chamber, each conical section on the shaft defining a shoulder engagable with each ratchet step in the bore.

10. A syringe for hypodermic injections comprising
a barrel defining a chamber and supporting a needle adapted for hypodermic injections in fluid communication with the chamber, the barrel including at least one ratchet means having at least one ratchet step facing in a direction away from the needle,
a guide member disposed within the chamber, the guide member having a flexible pawl member slidably engagable with the ratchet means in the chamber and engagable with each ratchet step therein, the guide member having a bore, the bore including at least one ratchet means having a ratchet step facing the needle, and
a plunger disposed within the chamber and including stem means extending through the bore, a flexible pawl element mounted on the stem and slidably engagable with each ratchet means on the guide member for movement in a first direction and engagable with each ratchet step on the guide member to prevent movement in the opposite direction.

* * * * *